(12) United States Patent
Mihara

(10) Patent No.: US 9,855,004 B2
(45) Date of Patent: Jan. 2, 2018

(54) DEVICES AND METHODS FOR MEASURING HAIR CONDITION

(71) Applicant: EMPIRE TECHNOLOGY DEVELOPMENT LLC, Wilmington, DE (US)

(72) Inventor: Masaaki Mihara, Chiba (JP)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 376 days.

(21) Appl. No.: 14/631,872

(22) Filed: Feb. 26, 2015

(65) Prior Publication Data
US 2016/0249849 A1    Sep. 1, 2016

(51) Int. Cl.
*G01N 21/84*    (2006.01)
*A61B 5/00*     (2006.01)
*A61B 17/00*    (2006.01)

(52) U.S. Cl.
CPC ............ *A61B 5/448* (2013.01); *A61B 5/0051* (2013.01); *A61B 5/0059* (2013.01); *A61B 5/443* (2013.01); *A61B 5/6838* (2013.01); *A61B 5/7282* (2013.01); *A61B 5/742* (2013.01); *A61B 2017/00876* (2013.01); *A61B 2503/40* (2013.01); *A61B 2562/12* (2013.01)

(58) Field of Classification Search
CPC ....... A61B 5/441; A61B 5/448; A61B 5/6838; A61B 2018/00452; A61B 2018/00476; G01N 2800/20
USPC .......... 73/760, 788, 800; 132/203, 207, 212; 356/428–440
See application file for complete search history.

(56) References Cited

U.S. PATENT DOCUMENTS

| 4,007,992 A |   | 2/1977  | Petrohilos et al. |
|-------------|---|---------|-------------------|
| 5,081,870 A |   | 1/1992  | Fitzgerald        |
| 5,167,150 A | * | 12/1992 | Shofner ................... G01N 3/08 356/429 |

(Continued)

FOREIGN PATENT DOCUMENTS

DE    102004037566 A1    3/2006

OTHER PUBLICATIONS

International Search Report and Written Opinion of the International Searching Authority, International application No. PCT/US2016/018998, dated Apr. 29, 2016.

(Continued)

*Primary Examiner* — Hoa Pham
(74) *Attorney, Agent, or Firm* — Turk IP Law, LLC

(57) ABSTRACT

Technologies are generally described for measuring hair condition using a hair condition measuring device. Example devices and systems described herein may include a first clamp, a second clamp, a vibrator, a laser beam source, a photodetector and/or a processor. The first claim may be configured to clamp a first end of hair, and the second clamp may be configured to clamp a second end of the hair, so that the hair is stretched between the first clamp and the second clamp. The laser beam source may be configured to generate a laser beam toward the hair. The photodetector may be configured to detect at least part of the laser beam reflected by the hair and convert an intensity of the detected part of the laser beam to an electrical signal. The processor may be configured to measure condition of the hair based on the electrical signal.

29 Claims, 11 Drawing Sheets

(56) References Cited

U.S. PATENT DOCUMENTS

| | | | |
|---|---|---|---|
| 5,617,210 | A | 4/1997 | Darbon et al. |
| 5,915,279 | A | 6/1999 | Cantrall et al. |
| 7,261,000 | B2 | 8/2007 | Sherman et al. |
| 7,928,739 | B2 | 4/2011 | Sherman et al. |
| 2006/0089555 | A1* | 4/2006 | Gummer .............. A61B 5/0059 600/476 |
| 2008/0068604 | A1 | 3/2008 | Grossinger et al. |
| 2008/0259322 | A1* | 10/2008 | Korotkov .............. A61B 5/0059 356/237.1 |
| 2015/0126981 | A1* | 5/2015 | Verghese ............. A61B 5/0059 606/9 |
| 2015/0173835 | A1* | 6/2015 | Moeskops ............ A61B 18/203 606/9 |
| 2017/0023528 | A1* | 1/2017 | Mihara .................. G01N 29/07 |
| 2017/0119130 | A1* | 5/2017 | Witchell ............. A45D 44/005 |

OTHER PUBLICATIONS

F.-J. Wortmann et al., "Analyzing the Laser-Light Reflection from Human Hair Fibers. II. Deriving a Measure of Hair Luster," Journal of Cosmetic Science, Jan. / Feb. 2004, pp. 81-93, vol. 55.

* cited by examiner

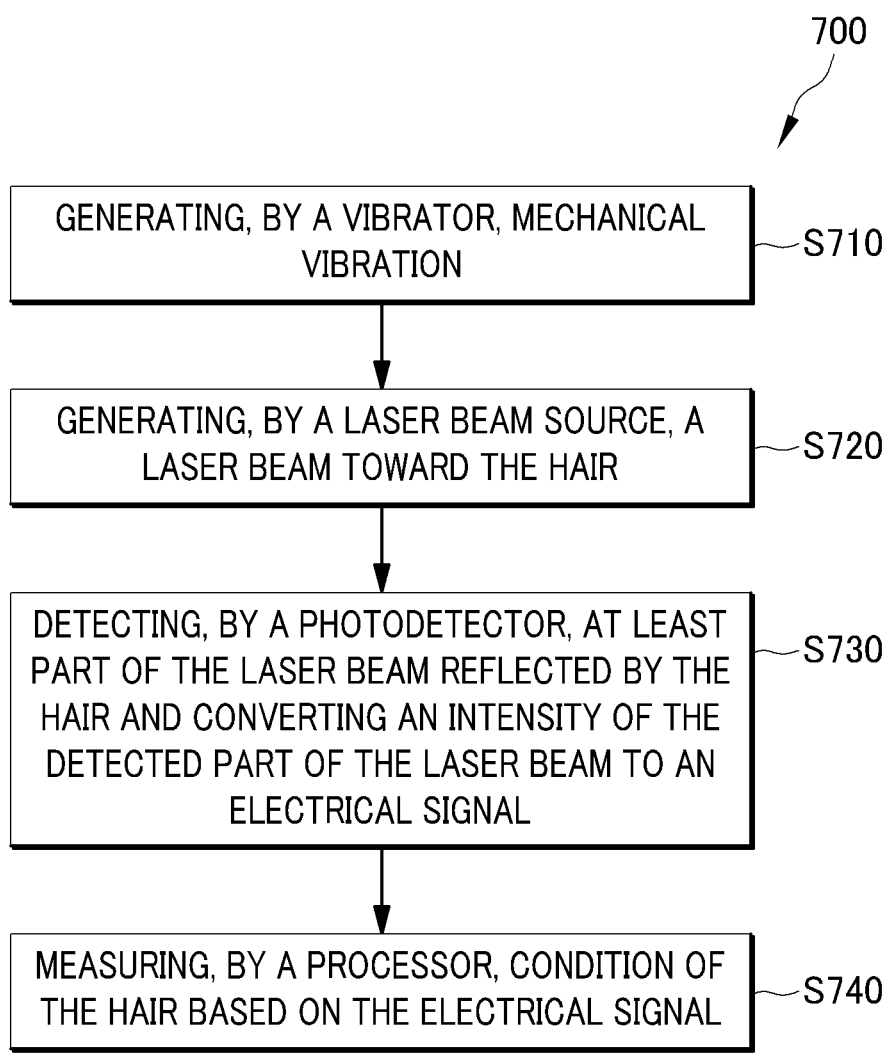

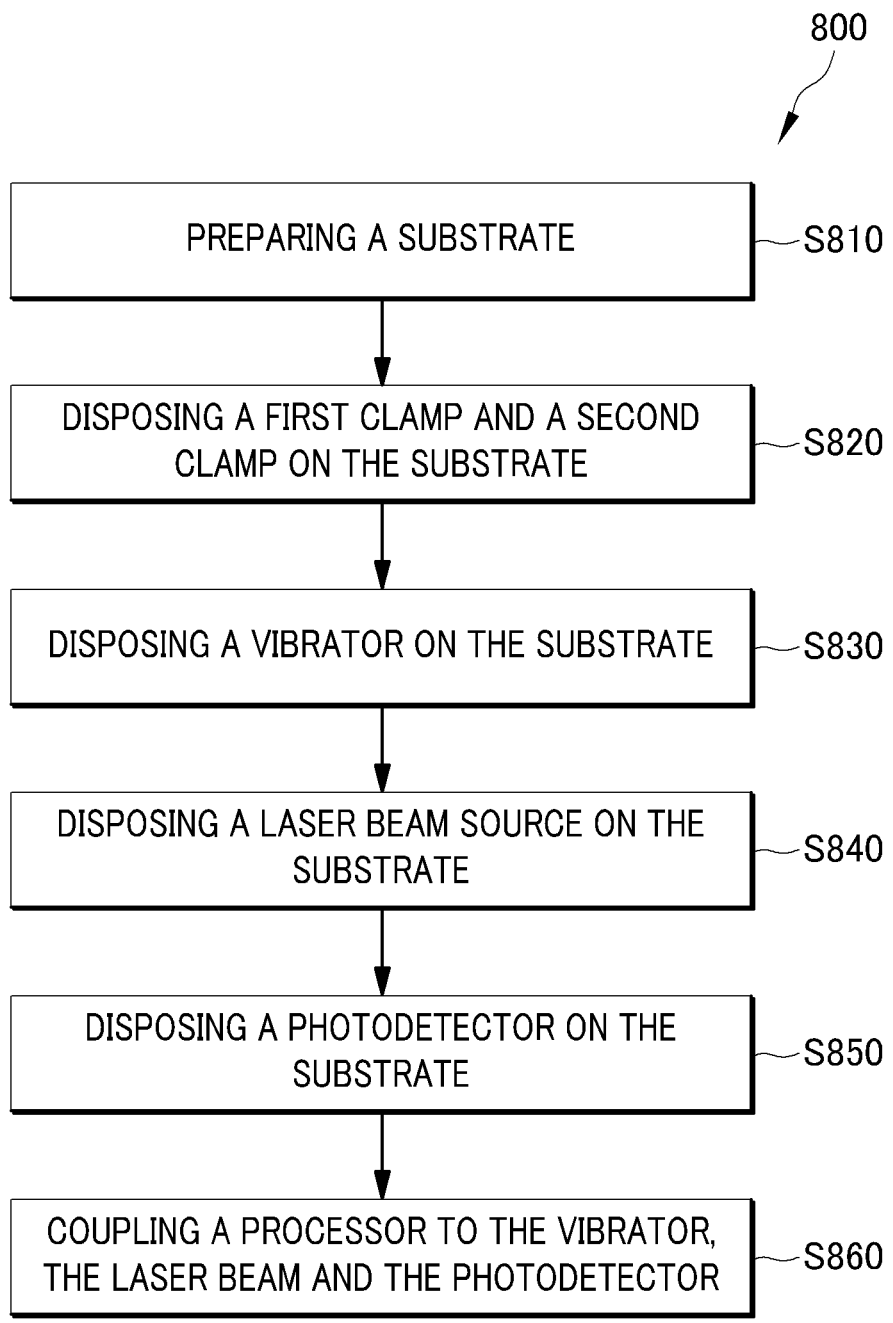

DEVICES AND METHODS FOR MEASURING HAIR CONDITION

BACKGROUND

Unless otherwise indicated herein, the approaches described in this section are not prior art to the claims in this application and are not admitted to be prior art by inclusion in this section.

Human or animal hair includes a cuticle that is the outermost part of the hair shaft. The hair cuticle is a hard shingle-like layer that provides the mechanical strength of the hair fiber and acts as a protective barrier for the hair softer inner structure including the medulla and cortex. A healthy cuticle provides not only a protective layer but also a structure that controls the moisture content of the hair fiber. The most of the shine or luster that makes healthy hair so attractive is maintained due to the cuticle. Such cuticles are often damaged by external mechanical treatment such as brushing, using heat or chemical processing. Also, environmental elements such as the sun or wind can cause wear and tear on the hair cuticles.

Accordingly, the cuticle condition of hair determines the health and cosmetic problems of the hair because the capability of hair for retaining its inner content and shine can be deteriorated when the cuticle is damaged through exposure to hair treatment and exposure to the natural environment. Accordingly, it is important to precisely measure the shine or luster of the hair cuticle to determine the overall health of hair so that one can assess possible cosmetic options and hair care options to maintain or improve the health of the hair. Also, the hair condition measurement will be desirable for all cosmetic applications including formulation, support of efficacy claim and efficacy testing of hair care products.

Hair condition measuring devices have been developed to detect the moisture content in hair, and have employed various techniques including a NIR (near infrared) moisture meter and Raman spectroscopy. The NIR moisture meter relies on the property of water that absorbs a specific wavelength of NIR light. However, it may be difficult to precisely measure the attenuation of the NIR light reflected from thin and fine hairs. Also, different levels of moisture at the surface and inner side of hair make the moisture measurement more challenging. The Raman spectroscopy relies on inelastic scattering of monochromatic light such as laser light irradiated on molecules of moisture in hair. For example, the laser light interacts with molecular vibrations, resulting in the energy of the laser photons being shifted upwards or downwards between a ground energy state and a virtual energy state. The shift in energy provides information about the vibrational modes to identify the molecules of moisture. Although the Raman spectroscopy provides decent precision of hair condition measurement, it is costly and may not be implemented in a portable size for individual users.

SUMMARY

Technologies generally described herein relate to measuring moisture in skin.

Various example apparatus configured to measure hair condition described herein may include one or more of a first clamp, a second clamp, a vibrator, a laser beam source, a photodetector and/or a processor. The first clamp may be configured to clamp a first end of hair. The second clamp may be configured to clamp a second end of the hair, so that the hair is stretched between the first clamp and the second clamp. The vibrator may be configured to generate mechanical vibration such that the mechanical vibration is imparted to the hair. The laser beam source may be configured to generate a laser beam toward the hair. The photodetector may be configured to detect at least part of the laser beam reflected by the hair and convert an intensity of the detected part of the laser beam to an electrical signal. The processor may be configured to measure condition of the hair based on the electrical signal.

In some examples, methods of measuring hair condition are described. Example methods may include generating, by a vibrator, mechanical vibration such that the mechanical vibration is imparted to hair being stretched between a first clamp and a second clamp. A laser beam may be generated, by a laser beam source, toward the hair. At least part of the laser beam reflected by the hair may be detected, by a photodetector, and an intensity of the detected part of the laser beam may be converted to an electrical signal. Condition of the hair may be measured, by a processor, based on the electrical signal.

In some examples, a computer-readable storage medium is described that may be adapted to store a program operable by a hair condition measuring device. The hair condition measuring device may include various features as further described herein. The program may include one or more instructions for generating, by a vibrator, mechanical vibration such that the mechanical vibration is imparted to hair being stretched between a first clamp and a second clamp, and generating, by a laser beam source, a laser beam toward the hair. The program may further include one or more instructions for detecting, by a photodetector, at least part of the laser beam reflected by the hair and converting an intensity of the detected part of the laser beam to an electrical signal, and measuring, by a processor, condition of the hair based on the electrical signal.

In some examples, methods of manufacturing a hair condition measuring device are described. Example methods may include disposing a first clamp and a second clamp on the substrate, such that the first clamp is spaced apart from the second clamp. The first clamp may be configured to clamp a first end of hair, and the second clamp may be configured to clamp a second end of the hair, so that the hair is stretched between the first clamp and the second clamp. A vibrator may be disposed on the substrate, the vibrator being configured to generate mechanical vibration such that the mechanical vibration is imparted to the hair. A photodetector may be disposed on the substrate, the photodetector being configured to detect at least part of the laser beam reflected by the hair and convert an intensity of the detected part of the laser beam to an electrical signal. A processor may be coupled to the vibrator, the laser beam and the photodetector, the processor being configured to measure condition of the hair based on the electrical signal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 7 illustrates an example flow diagram of a method adapted to measure hair condition;

FIG. 8 illustrates an example flow diagram of a method adapted to manufacture a hair condition measuring device;

DETAILED DESCRIPTION

Figure 1:
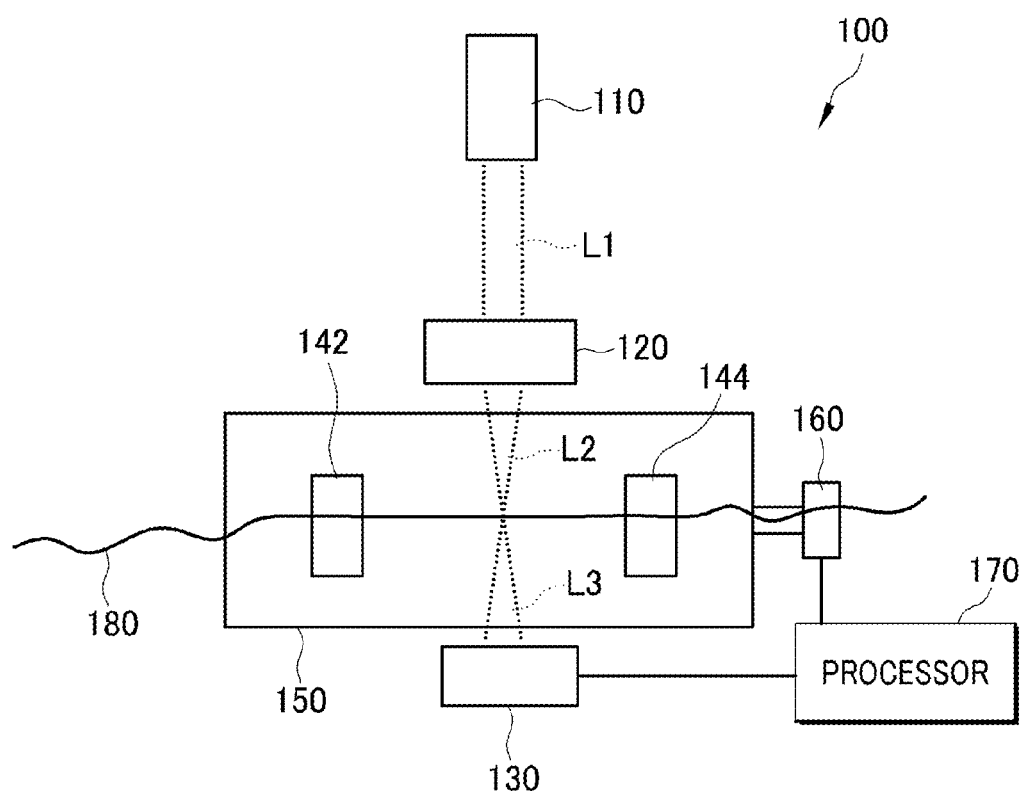
FIG. 1 schematically shows a block diagram of an example hair condition measuring device configured to measure at least part of a laser beam reflected by hair.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices and computer program products related to measuring hair condition.

Briefly stated, technologies are generally described for measuring hair condition using a hair condition measuring device. Example devices and systems described herein may include one or more of a first clamp, a second clamp, a vibrator, a laser beam source, a photodetector and/or a processor. The first clamp may be arranged on a substrate to be spaced apart from the second clamp. The first claim may be configured to clamp a first end of hair, and the second clamp may be configured to clamp a second end of the hair, so that the hair is stretched between the first clamp and the second clamp. The vibrator may be, for example, a magnetic vibrator including a magnet at least partially disposed inside a coil, where the magnet may be configured to oscillate within the coil when an alternating current is applied to the coil and thus impart mechanical vibration to the hair. The laser beam source may be configured to generate a laser beam (e.g., laser beam with a wavelength of about 650 nm) toward the hair. The photodetector may be configured to detect at least part of the laser beam reflected by the hair and convert an intensity of the detected part of the laser beam to an electrical signal. The processor (e.g., a microprocessor) may be coupled to the vibrator, the laser beam and the photodetector, and may be configured to measure condition of the hair based on the electrical signal. In some embodiments, the processor may measure the condition of the hair by comparing a peak value of the electrical signal to a reference value, or based on a value resulting from integrating noise components of the electrical signal.

FIG. 1 schematically shows a block diagram of an example hair condition measuring device configured to measure at least part of a laser beam reflected by hair, arranged in accordance with at least some embodiments described herein. As depicted, a hair condition measuring device 100 may include one or more of a laser beam source 110, an object lens 120, a photodetector 130, a first clamp 142, a second clamp 144, a vibration table 150, a vibrator 160 and/or a processor 170.

In some embodiments, first clamp 142 and second clamp 144 may be arranged on vibration table 150 to be spaced apart from each other. First clamp 142 may be configured to clamp a first end of hair 180, and second clamp 144 may be configured to clamp a second end of hair 180, so that hair 180 is stretched between first and second clamps 142 and 144. For example, each of first and second clamps 142 and 144 may be implemented using a rubber block on which a slit may be formed to clamp one end of hair 180. In some embodiments, hair 180 may be a human hair or an animal hair such as wool, mohair, cashmere, angora, fleece, fur or a combination thereof. Also, animal hair may be a hair of various animals, for example, human, sheep, goat, rabbit, etc.

In some embodiments, vibrator 160 may be electrically coupled to processor 170, which may be configured to control vibrator 160 to generate mechanical vibration such that the mechanical vibration is imparted to hair 180 through vibration table 150. For example, vibrator 160 may be a magnetic vibrator including a magnet at least partially disposed inside a coil, wherein the magnet is configured to oscillate within the coil when an alternating current is applied to the coil and thereby impart the mechanical vibration to hair 180. In another example, vibrator 160 may be an electrical vibrator including an electric motor and an off-center weight which may be configured to vibrate when the motor spins. Such electrical vibrator may be further configured to be controlled by an external device (for example, a smartphone, a cellular phone, etc.) and/or a software program (for example, an application installed in a smartphone). Alternatively, vibrator 160 may be a linear actuator using an ultrasonic motor.

In operation, laser beam source 110 may generate a laser beam L1 toward hair 180 through object lens 120, which may be configured to focus laser beam L1 so that focused laser beam L2 on a part of hair 180. For example, the laser beam generated from laser beam source 110 may be a laser beam with a wavelength in the visible spectrum, e.g., about 650 nm. In some other examples, the laser beam may be a laser beam with a wavelength in the ultraviolet or infrared spectrum. In an alternative embodiment, a LED (light-emitting device) or collimator light source may be used instead of laser beam source 110. At least part L3 of laser beam L2 may be reflected by hair 180 (for example, cuticle layer of hair 180) and may be detected by photodetector 130. For example, photodetector 130 may be implemented using various types of photodetectors or image sensors including, but not limited to, a CMOS (complementary metal-oxide-semiconductor) sensor, a CCD (charge-coupled device) sensor, a photodiode, etc. Photodetector 130 may be configured to convert an intensity of detected part L3 of the laser beam to an electrical signal. Processor 170 (for example, a microprocessor) may be electrically coupled to photodetector 130, such that processor 170 may measure condition of hair 180 based on the electrical signal generated by photodetector 130.

If hair 180 is in a healthy condition (for example, the cuticle layer of hair 180 is not damaged and hair 180 has uniform thickness along its longitudinal direction), laser beam L3 reflected by hair 180 may have a substantially uniform intensity. On the other hand, if the cuticle layer of hair 180 is partially damaged or has non-uniform thickness due to such damaged portion, laser beam L3 reflected by hair 180 may have non-uniform intensity or a number of noise components. Accordingly, processor 170 may measure condition of hair 180 based on a value of the electrical signal generated by photodetector 130, which is converted from the intensity of laser beam L3.

In some instances, when hair 180 is stretched between first and second clamps 142 and 144, hair 180 may be vibrated in its string state at a high frequency. The vibration of the hair string may cause noise components to be unnecessarily incorporated in laser beam L3 reflected by hair 180, which can deteriorate the accuracy of the hair condition measurement by processor 170. To cancel such vibration of the hair string, vibrator 160 may be controlled to generate mechanical vibration at a low frequency, such that the mechanical vibration is imparted to hair 180 through vibration table 150.

In some embodiments, processor 170 may be further configured to measure the condition of hair 180 by comparing a peak value of the electrical signal to a reference value. The peak value of the electrical signal may refer to a peak value of amplitude or power of the electrical signal. Alternatively or additionally, processor 170 may be further configured to measure the condition of hair 180 based on a value resulting from integrating noise components of the electrical signal, in which the noise components may be indicative of vibration of the hair 180.

In some embodiments, hair condition measuring device 100 may further include a display unit (not shown). The display unit may be configured to display at least one of the electrical signal generated by photodetector 130 or a value indicating the condition of hair 180 which may be generated by processor 170.

Figure 2A:
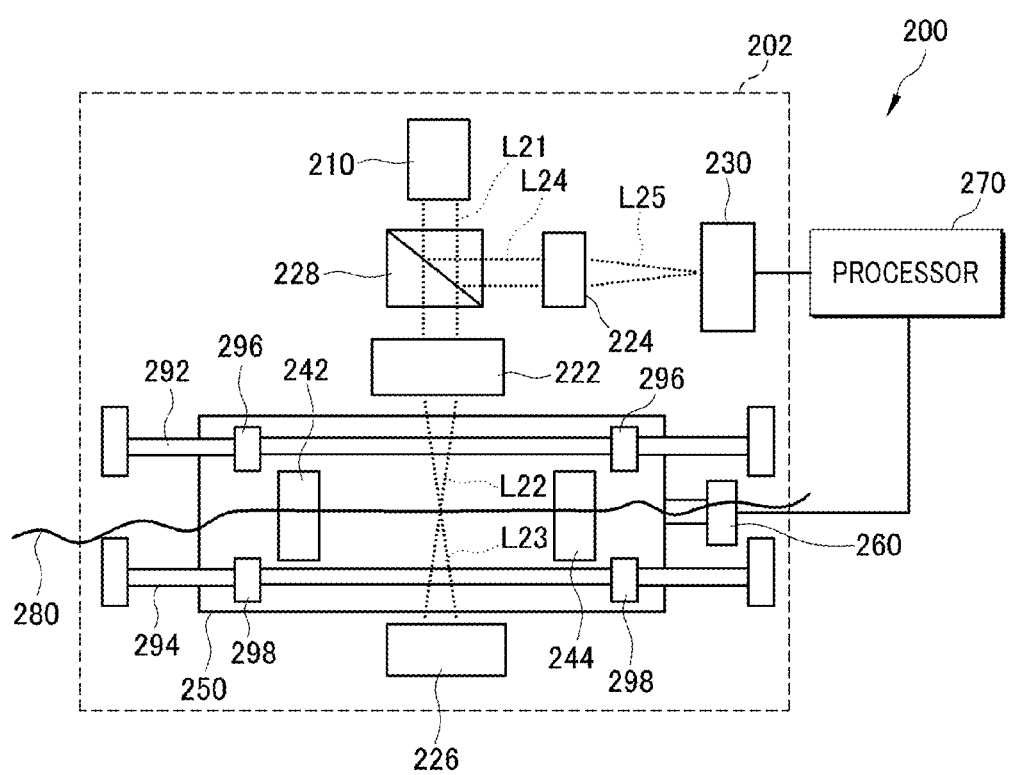
FIGS. 2A and 2B schematically show top and side views of another example hair condition measuring device configured to measure at least part of a laser beam reflected by hair.
Figure 2B:
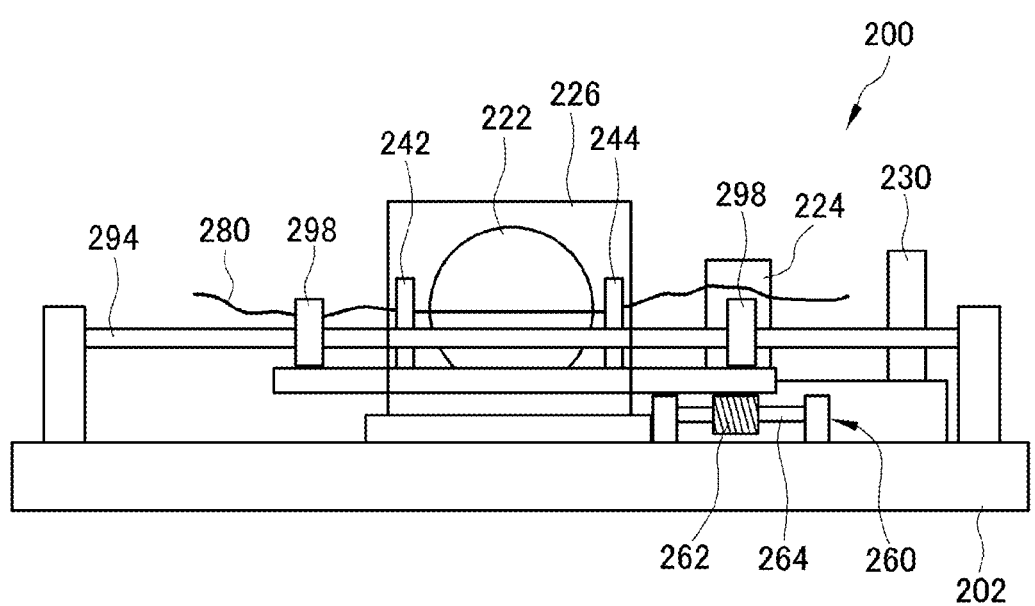

FIGS. 2A and 2B schematically show top and side views of another example hair condition measuring device configured to measure at least part of a laser beam reflected by hair, arranged in accordance with at least some embodiments described herein. As depicted, a hair condition measuring device 200 may include one or more of a laser beam source 210, object lenses 222 and 224, a one-way mirror 226, a beam splitter 228, a photodetector 230, a first clamp 242, a second clamp 244, a vibration table 250, a vibrator 260 and/or a processor 270. One or more of above-described elements or units 210 to 270 may be disposed on a substrate 202.

In some embodiments, vibration table 250 may include sliding rods 292 and 294, and sliding support members 296 and 298 having through-holes, respectively, through which sliding rods may slide. Specifically, sliding rods 292 and 294 may be configured to slide through sliding support members 296 and 298, respectively, for example, according to the movement of vibration table 250 by a user (in a horizontal direction when viewed from the top view of FIG. 2A).

In some embodiments, first clamp 242 and second clamp 244 may be arranged on vibration table 250 to be spaced apart from each other. First clamp 242 may be configured to clamp a first end of hair 280, and second clamp 244 may be configured to clamp a second end of hair 280, so that hair 280 is stretched between first and second clamps 242 and 244. For example, each of first and second clamps 242 and 244 may be implemented using a rubber block on which a slit may be formed to clamp one end of hair 280. In some embodiments, hair 280 may be a human hair or an animal hair such as wool, mohair, cashmere, angora, fleece, fur or a combination thereof. Also, animal hair may be a hair of various animals, for example, human, sheep, goat, rabbit, etc.

In some embodiments, vibrator 260 may be electrically coupled to processor 270, which may be configured to control vibrator 260 to generate mechanical vibration such that the mechanical vibration is imparted to hair 280 through vibration table 250. As illustrated in FIG. 2B, vibrator 260 may be a magnetic vibrator including a magnet 264 at least partially disposed inside a coil 262, wherein magnet 264 is configured to oscillate within coil 262 when an alternating current is applied to coil 262 (for example, by processor 270) and thereby impart the mechanical vibration to hair 280. In another example, vibrator 260 may be an electrical vibrator including an electric motor and an off-center weight which may be configured to vibrate when the motor spins. Such electrical vibrator may be further configured to be controlled by an external device (for example, a smartphone, a cellular phone, etc.) and/or a software program (for example, an application installed in a smartphone).

In operation, laser beam source 210 may generate a laser beam L21 toward hair 280 through object lens 222, which may be configured to focus laser beam L21 so that focused laser beam L22 on a part of hair 280. For example, the laser beam generated from laser beam source 210 may be a laser beam with a wavelength of about 650 nm. At least part L23 of laser beam L22 may be reflected by hair 280 (for example, cuticle layer of hair 280) and may be propagated towards a one-way mirror 226, which may be configured to reflect at least part of laser beam L23 reflected by hair 280. The part of laser beam L23 reflected by one-way mirror 226 may be then propagated towards beam splitter 228. Object lens 224 may be configured to receive laser beam L24 reflected by beam splitter 226 and focus the received laser beam (that is, laser beam L25) on photodetector 230. For example, photodetector 230 may be implemented using various types of photodetectors or image sensors including, but not limited to, a CMOS sensor, a CCD sensor, a photodiode, etc. Photodetector 230 may be configured to convert an intensity of detected part L25 of the laser beam to an electrical signal. Processor 270 (for example, a microprocessor) may be electrically coupled to photodetector 230, such that processor 270 may measure condition of hair 280 based on the electrical signal generated by photodetector 230.

If hair 280 is in a healthy condition (for example, the cuticle layer of hair 280 is not damaged and hair 180 has uniform thickness along its longitudinal direction), laser beam L25 reflected by beam splitter 226 may have a substantially uniform intensity. On the other hand, if the cuticle layer of hair 280 is partially damaged or has non-uniform thickness due to such damaged portion, laser beam L25 may have non-uniform intensity or a number of noise components. Accordingly, processor 270 may measure condition of hair 280 based on a value of the electrical signal generated by photodetector 230, which is converted from the intensity of laser beam L25.

In some instances, when hair 280 is stretched between first and second clamps 242 and 244, hair 280 may be vibrated in its string state at a high frequency. The vibration of the hair string may cause noise components to be unnecessarily incorporated in the laser beam reflected by hair 280, which can deteriorate the accuracy of the hair condition measurement by processor 270. To cancel such vibration of the hair string, vibrator 260 may be controlled to generate mechanical vibration at a low frequency, such that the mechanical vibration is imparted to hair 280 through vibration table 250.

In some embodiments, processor 270 may be further configured to measure the condition of hair 280 by comparing a peak value of the electrical signal to a reference value. The peak value of the electrical signal may refer to a peak value of amplitude or power of the electrical signal. Alternatively or additionally, processor 270 may be further configured to measure the condition of hair 280 based on a value resulting from integrating noise components (for example, a frequency response) of the electrical signal.

In some embodiments, hair condition measuring device 200 may further include a display unit (not shown). The display unit may be configured to display at least one of the electrical signal generated by photodetector 230 or a value indicating the condition of hair 280 which may be generated by processor 270.

Figure 3:
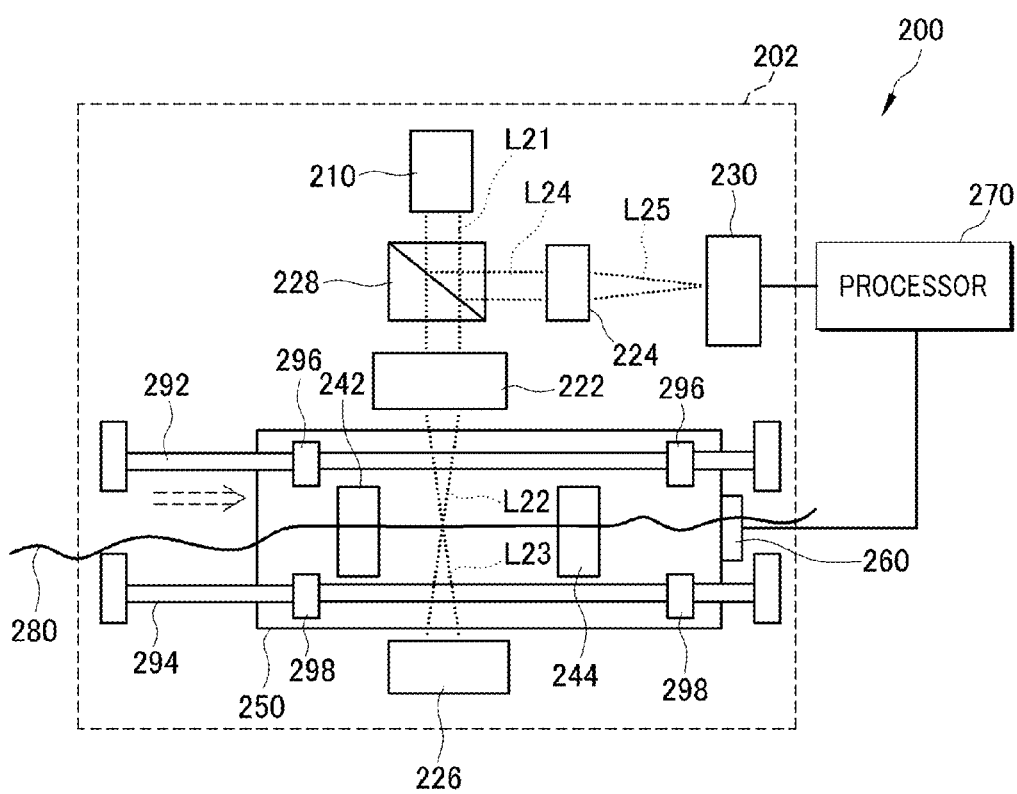
FIG. 3 schematically shows the example hair condition measuring device as illustrated in FIGS. 2A and 2B, where a vibration table is laterally moving for adjusting a laser beam to be irradiated on different parts of hair.

FIG. 3 schematically shows the example hair condition measuring device as illustrated in FIGS. 2A and 2B, where a vibration table is laterally moving for adjusting a laser beam to be irradiated on different parts of hair, arranged in accordance with at least some embodiments described herein.

In some embodiments, vibration table 250 may be moved laterally for adjusting a laser beam to be irradiated on different parts of hair 280. As illustrated in FIG. 3, vibration table 250 may be moved automatically (for example, by using a linear motor) or manually (for example, by a user or an operator) rightward or leftward so that laser beam L22 can be focused on a different part of hair 280. Such operation of moving vibration table 250 facilitates the measurement of hair condition on various parts of hair 280.

Figure 4A:
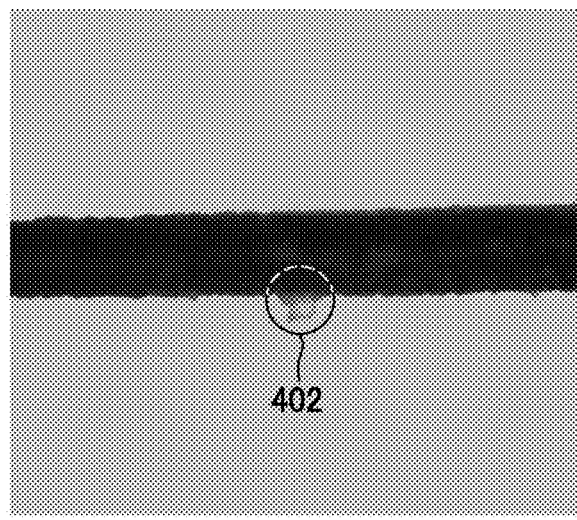
FIG. 4A shows a picture of hair with its cuticle being partially damaged.
Figure 4B:
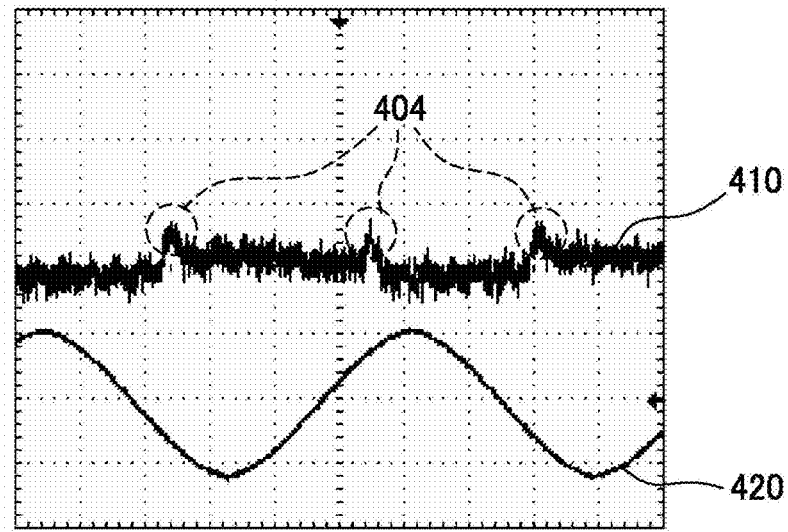
FIG. 4B illustrates a graph showing a vibration frequency used in vibrating the hair and a detected intensity of the laser beam reflected by the hair.

FIG. 4A shows a picture of hair with its cuticle being partially damaged, and FIG. 4B illustrates a graph showing a vibration frequency 420 used in vibrating the hair and a detected intensity of the laser beam reflected by the hair, which are arranged in accordance with at least some embodiments described herein.

As depicted, when a cuticle layer of hair is partially damaged (for example, as indicated by a circle 402 in FIG. 4A), a detected intensity 410 of the laser beam reflected by the hair according to the above embodiments as illustrated in FIGS. 1 to 3 may intermittently have some peak values 404. Accordingly, a hair condition measuring device such as hair condition measuring device 100 or 200 may determine that the hair is not in a healthy condition, when at least one of peak values 404 is greater than a reference value.

Figure 5A:
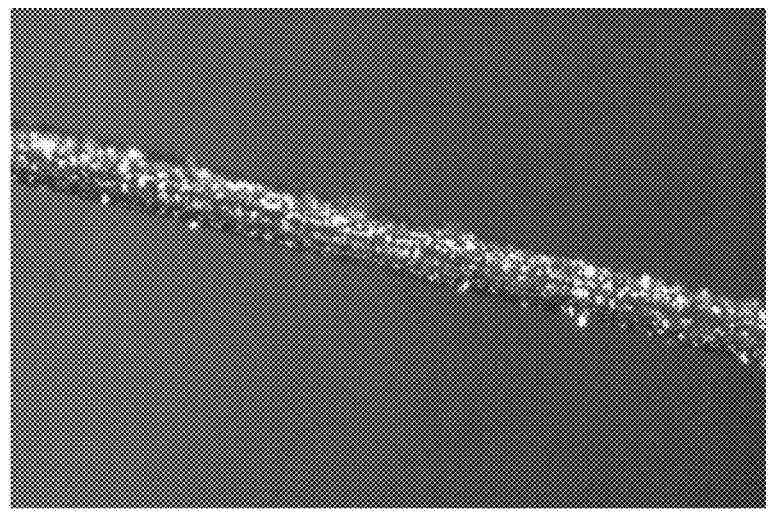
FIG. 5A shows a picture of hair with its cuticle being damaged due to friction.
Figure 5B:
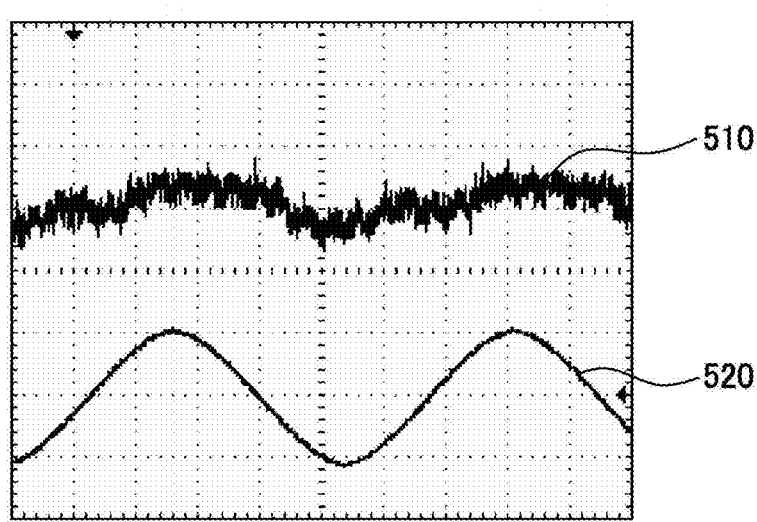
FIG. 5B illustrates a graph showing a vibration frequency used in vibrating the hair and a detected intensity of the laser beam reflected by the hair.

FIG. 5A shows a picture of hair with its cuticle being damaged due to friction, and FIG. 5B illustrates a graph showing a vibration frequency 520 used in vibrating the hair and a detected intensity of the laser beam reflected by the hair, which are arranged in accordance with at least some embodiments described herein.

As depicted, when a cuticle layer of hair is damaged and thus has non-uniform thickness along its longitudinal direction, a detected intensity 510 of the laser beam reflected by the hair according to the above embodiments as illustrated in FIGS. 1 to 3 may have substantially non-uniform values over time and/or have a number of noise components. Accordingly, a hair condition measuring device such as hair condition measuring device 100 or 200 may determine that the hair is not in a healthy condition, based on a value resulting from integrating noise components of the detected intensity.

Figure 6A:
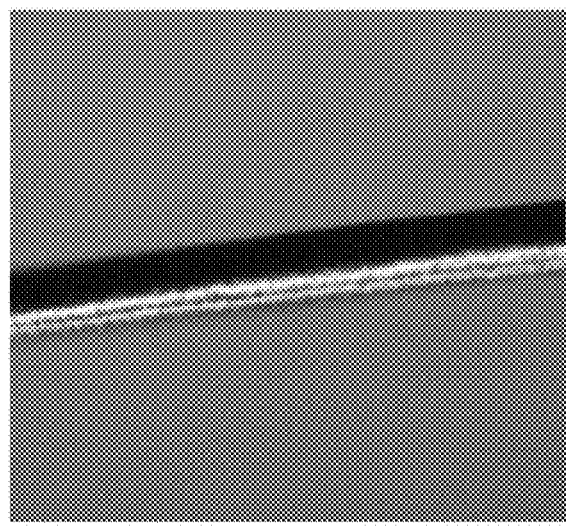
FIG. 6A shows a picture of hair with its cuticle in a good condition.
Figure 6B:
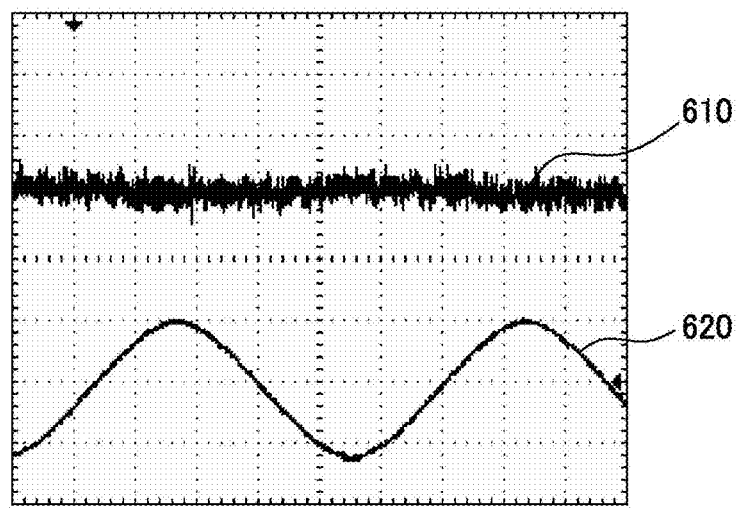
FIG. 6B illustrates a graph showing a vibration frequency used in vibrating the hair and a detected intensity of the laser beam reflected by the hair.

FIG. 6A shows a picture of hair with its cuticle in a good condition, and FIG. 6B illustrates a graph showing a vibration frequency 620 used in vibrating the hair and a detected intensity of the laser beam reflected by the hair, which are arranged in accordance with at least some embodiments described herein.

As depicted, when a cuticle layer of hair is not damaged and thus has uniform thickness along its longitudinal direction, a detected intensity 610 of the laser beam reflected by the hair according to the above embodiments as illustrated in FIGS. 1 to 3 may have substantially uniform values over time. In such case, a hair condition measuring device such as hair condition measuring device 100 or 200 may determine that the hair is in a healthy condition.

FIG. 7 illustrates an example flow diagram of a method adapted to measure hair condition, arranged in accordance with at least some embodiments described herein. An example method 700 in FIG. 7 may be implemented using, for example, a computing device including a processor adapted to measure hair condition.

Method 700 may include one or more operations, actions, or functions as illustrated by one or more of blocks S710, S720, S730 and/or S740. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 700 may begin at block S710, "GENERATING, BY A VIBRATOR, MECHANICAL VIBRATION."

At block S710, mechanical vibration may be generated by a vibration. As depicted in FIG. 1, vibrator 160 may be electrically coupled to processor 170, which may be configured to control vibrator 160 to generate mechanical vibration such that the mechanical vibration is imparted to hair 180 through vibration table 150. In some embodiments, to cancel the vibration of hair 180 in its string state that may cause unnecessary noise components to be incorporated in a laser beam such as laser beam L3 reflected by hair 180, vibrator 160 may be controlled to generate mechanical vibration at a low frequency, such that the low-frequency mechanical vibration is imparted to hair 180 through vibration table 150. Block S710 may be followed by block S720, "GENERATING, BY A LASER BEAM SOURCE, A LASER BEAM TOWARD THE HAIR."

At block S720, a laser beam may be generated, by a laser beam source, toward the hair. As illustrated in FIG. 1, laser beam source 110 may generate a laser beam L1 toward hair 180 through object lens 120, which may be configured to focus laser beam L1 so that focused laser beam L2 on a part of hair 180. Block S720 may be followed by block S730, "DETECTING, BY A PHOTODETECTOR, AT LEAST PART OF THE LASER BEAM REFLECTED BY THE HAIR AND CONVERTING AN INTENSITY OF THE DETECTED PART OF THE LASER BEAM TO AN ELECTRICAL SIGNAL."

At block S730, at least part of the laser beam reflected by the hair may be detected, by a photodetector, and an intensity of the detected part of the laser beam may be converted to an electrical signal. As illustrated in FIG. 1, at least part L3 of laser beam L2 may be reflected by hair 180 (for example, cuticle layer of hair 180) and may be detected by photodetector 130. Photodetector 130 may be configured to convert an intensity of detected part L3 of the laser beam to an electrical signal. Block S730 may be followed by block S740, "MEASURING, BY A PROCESSOR, CONDITION OF THE HAIR BASED ON THE ELECTRICAL SIGNAL."

At block S740, condition of the hair may be measured, by a processor, based on the electrical signal. As depicted in FIG. 1, processor 170 (for example, a microprocessor) may be electrically coupled to photodetector 130, such that processor 170 may measure condition of hair 180 based on the electrical signal generated by photodetector 130. If the hair is in a healthy condition (for example, the cuticle layer of the hair is not damaged and the hair has uniform thickness along its longitudinal direction), a laser beam reflected by the hair may have a substantially uniform intensity. On the other hand, if the cuticle layer of the hair is partially damaged or has non-uniform thickness due to such damaged portion, the laser beam reflected by the hair may have non-uniform intensity or a number of noise components. Accordingly, the condition of the hair may be measured based on a value of the electrical signal generated by the photodetector, which is converted from the intensity of the laser beam reflected by the hair.

In some embodiments, the condition of the hair may be measured by comparing a peak value of the electrical signal to a reference value. The peak value of the electrical signal may refer to a peak value of amplitude or power of the electrical signal. Alternatively or additionally, the condition of the hair may be measured based on a value resulting from integrating noise components (for example, a frequency response) of the electrical signal.

FIG. 8 illustrates an example flow diagram of a method adapted to manufacture a hair condition measuring device, arranged in accordance with at least some embodiments described herein. An example method 800 in FIG. 8 may be implemented using, for example, a computing device including a processor adapted to control manufacturing of a hair condition measuring device.

Method 800 may include one or more operations, actions, or functions as illustrated by one or more of blocks S810, S820, S830, S840, S850 and/or S860. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 800 may begin at block S810, "PREPARING A SUBSTRATE."

At block S810, a substrate may be prepared. As illustrated in FIGS. 2A and 2B, substrate 202 may be prepared. Block S810 may be followed by block S820, "DISPOSING A FIRST CLAMP AND A SECOND CLAMP ON THE SUBSTRATE."

At block S820, a first clamp and a second clamp may be disposed on the substrate. As illustrated in FIGS. 2A and 2B, first clamp 242 and second clamp 244 may be disposed on vibration table 250, which may be disposed on substrate 202. In some embodiments, first clamp 242 and second clamp 244 may be arranged on vibration table 250 to be spaced apart from each other. First clamp 242 may be configured to clamp a first end of hair 280, and second clamp 244 may be configured to clamp a second end of hair 280, so that hair 280 is stretched between first and second clamps 242 and 244. Block S820 may be followed by block S830, "DISPOSING A VIBRATOR ON THE SUBSTRATE."

At block 830, a vibrator may be disposed on the substrate. As illustrated in FIGS. 2A and 2B, vibrator 260 may be disposed on substrate 202. Vibrator 260 may be electrically coupled to processor 270, which may be configured to control vibrator 260 to generate mechanical vibration such that the mechanical vibration is imparted to hair 280 through vibration table 250. As illustrated in FIG. 2B, vibrator 260 may be a magnetic vibrator including a magnet 264 at least partially disposed inside a coil 262, wherein magnet 264 is configured to oscillate within coil 262 when an alternating current is applied to coil 262 (for example, by processor 270) and thereby impart the mechanical vibration to hair 280. Block S830 may be followed by block S840, "DISPOSING A LASER BEAM SOURCE ON THE SUBSTRATE."

At block S840, a laser beam source may be disposed on the substrate. As illustrated in FIGS. 2A and 2B, laser beam source 210 may be disposed on substrate 202. In some embodiments, laser beam source 210 may be configured to generate a laser beam L21 toward hair 280 through object lens 222, which may be configured to focus laser beam L21 so that focused laser beam L22 on a part of hair 280. For example, the laser beam generated from laser beam source 210 may be a laser beam with a wavelength of about 650 nm. At least part L23 of laser beam L22 may be reflected by hair 280 (for example, cuticle layer of hair 280) and may be propagated towards a one-way mirror 226, which may be configured to reflect at least part of laser beam L23 reflected by hair 280. The part of laser beam L23 reflected by one-way mirror 226 may be then propagated towards beam splitter 228. Object lens 224 may be configured to receive laser beam L24 reflected by beam splitter 226 and focus the received laser beam (that is, laser beam L25) on photodetector 230. Block S840 may be followed by block S850, "DISPOSING A PHOTODETECTOR ON THE SUBSTRATE."

At block S850, a photodetector may be disposed on the substrate. As illustrated in FIGS. 2A and 2B, photodetector 230 may be disposed on substrate 202. In some embodiments, photodetector 230 may be configured to convert an intensity of detected part L25 of the laser beam to an electrical signal. Block S850 may be followed by block S860, "COUPLING A PROCESSOR TO THE VIBRATOR, THE LASER BEAM AND THE PHOTODETECTOR."

At block S860, a processor may be coupled to the vibrator, the laser beam source and the photodetector. As depicted in FIGS. 2A and 2B, processor 270 may be coupled to vibrator 260, laser beam source 210 and photodetector 230. In some embodiments, processor 270 (for example, a microprocessor) may be electrically coupled to photodetector 230, such that processor 270 may measure condition of hair 280 based on the electrical signal generated by photodetector 230. In some embodiments, processor 270 may be further configured to measure the condition of hair 280 by comparing a peak value of the electrical signal to a reference value. The peak value of the electrical signal may refer to a peak value of amplitude or power of the electrical signal. Alternatively or additionally, processor 270 may be further configured to measure the condition of hair 280 based on a value resulting from integrating noise components (for example, a frequency response) of the electrical signal.

In light of the present disclosure, one skilled in the art will appreciate that, for this and other methods disclosed herein, the functions performed in the methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 9:
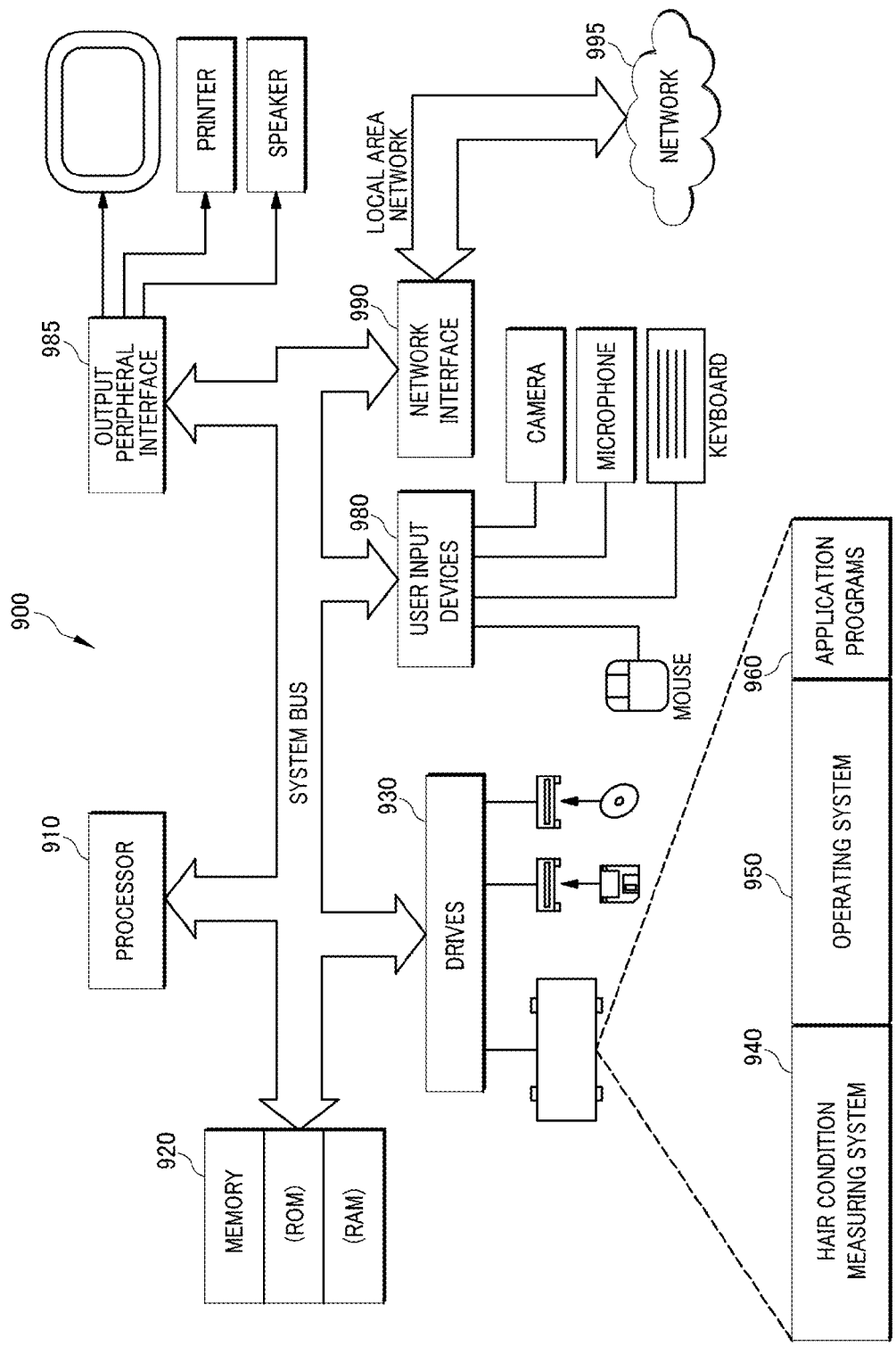
FIG. 9 shows a schematic block diagram illustrating an example computing system that can be configured to implement methods for measuring hair condition.

FIG. 9 shows a schematic block diagram illustrating an example computing system that can be configured to implement methods for measuring hair condition, arranged in accordance with at least some embodiments described herein. As depicted in FIG. 9, a computer 900 may include a processor 910, a memory 920 and one or more drives 930. Computer 900 may be implemented as a conventional computer system, an embedded control computer, a laptop, or a server computer, a mobile device, a set-top box, a kiosk, a vehicular information system, a mobile telephone, a customized machine, or other hardware platform.

Drives 930 and their associated computer storage media may provide storage of computer readable instructions, data structures, program modules and other data for computer 900. Drives 930 may include a hair condition measuring system 940, an operating system (OS) 950, and application programs 960. Hair condition measuring system 940 may be adapted to control a hair condition measuring device in such a manner as described above with respect to FIGS. 1 to 8.

Computer 900 may further include user input devices 980 through which a user may enter commands and data. Input devices can include an electronic digitizer, a camera, a microphone, a keyboard and pointing device, commonly referred to as a mouse, trackball or touch pad. Other input devices may include a joystick, game pad, satellite dish, scanner, or the like.

These and other input devices can be coupled to processor 910 through a user input interface that is coupled to a system bus, but may be coupled by other interface and bus structures, such as a parallel port, game port or a universal serial bus (USB). Computers such as computer 900 may also include other peripheral output devices such as display devices, which may be coupled through an output peripheral interface 985 or the like.

Computer 900 may operate in a networked environment using logical connections to one or more computers, such as a remote computer coupled to a network interface 990. The remote computer may be a personal computer, a server, a router, a network PC, a peer device or other common network node, and can include many or all of the elements described above relative to computer 900.

Networking environments are commonplace in offices, enterprise-wide area networks (WAN), local area networks (LAN), intranets, and the Internet. When used in a LAN or WLAN networking environment, computer 900 may be coupled to the LAN through network interface 990 or an adapter. When used in a WAN networking environment, computer 900 typically includes a modem or other means for establishing communications over the WAN, such as the Internet or a network 995. The WAN may include the Internet, the illustrated network 995, various other networks, or any combination thereof. It will be appreciated that other mechanisms of establishing a communications link, ring, mesh, bus, cloud, or network between the computers may be used.

In some embodiments, computer 900 may be coupled to a networking environment. Computer 900 may include one or more instances of a physical computer-readable storage medium or media associated with drives 930 or other storage devices. The system bus may enable processor 910 to read code and/or data to/from the computer-readable storage media. The media may represent an apparatus in the form of storage elements that are implemented using any suitable technology, including but not limited to semiconductors, magnetic materials, optical media, electrical storage, electrochemical storage, or any other such storage technology. The media may represent components associated with memory 920, whether characterized as RAM, ROM, flash, or other types of volatile or nonvolatile memory technology. The media may also represent secondary storage, whether implemented as storage drives 930 or otherwise. Hard drive implementations may be characterized as solid state, or may include rotating media storing magnetically encoded information.

Processor 910 may be constructed from any number of transistors or other circuit elements, which may individually or collectively assume any number of states. More specifically, processor 910 may operate as a state machine or finite-state machine. Such a machine may be transformed to a second machine or specific machine by loading executable instructions. These computer-executable instructions may transform processor 910 by specifying how processor 910 transitions between states, thereby transforming the transistors or other circuit elements constituting processor 910 from a first machine to a second machine. The states of either machine may also be transformed by receiving input from user input devices 980, network interface 990, other peripherals, other interfaces, or one or more users or other actors. Either machine may also transform states, or various physical characteristics of various output devices such as printers, speakers, video displays, or otherwise.

Figure 10:
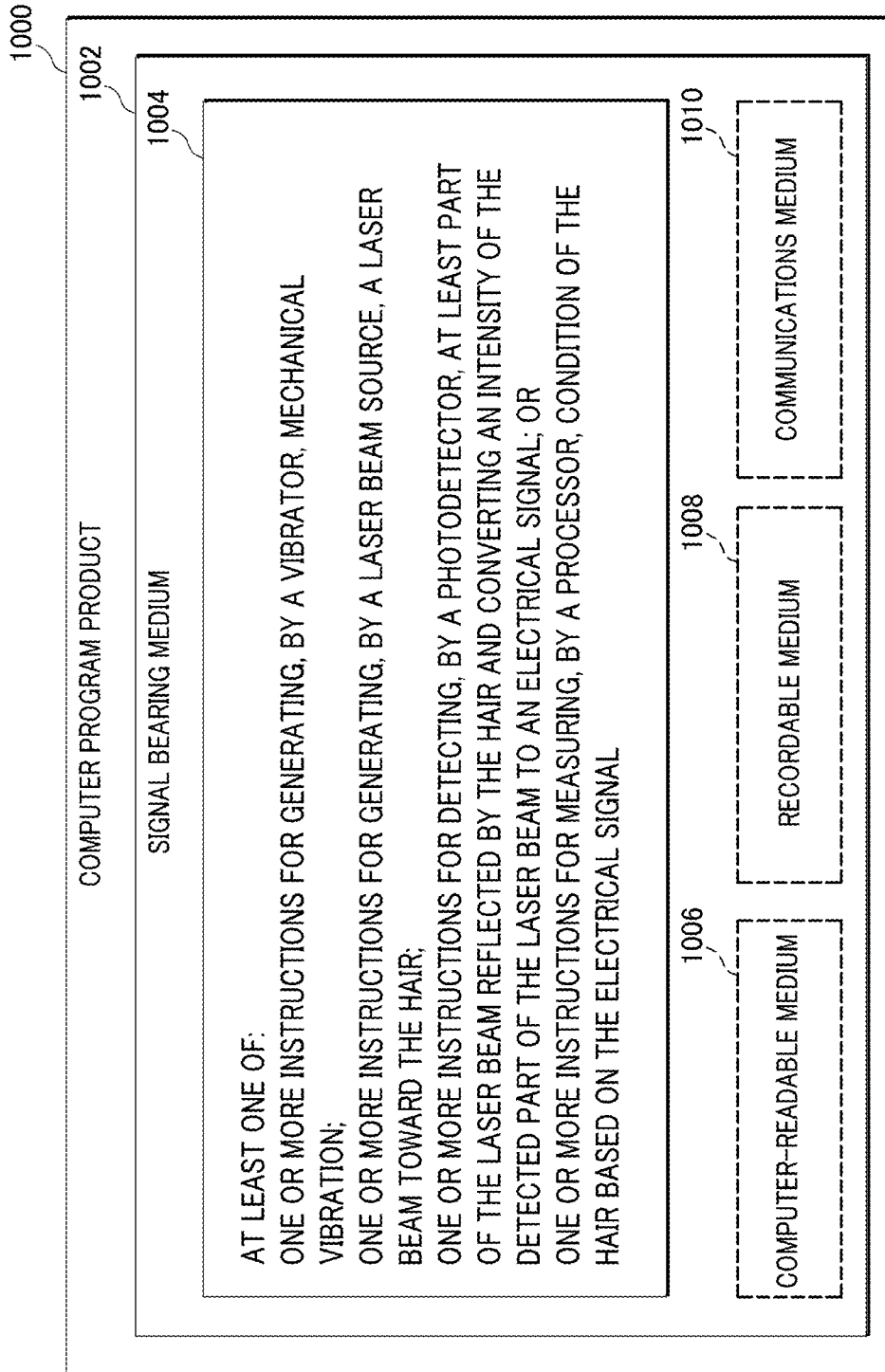
FIG. 10 illustrates computer program products that can be utilized to measure hair condition, all arranged in accordance with at least some embodiments described herein.

FIG. 10 illustrates computer program products that can be utilized to measure hair condition, in accordance with at least some embodiments described herein. Computer program product 1000 may include a signal bearing medium 1002. Signal bearing medium 1002 may include one or more instructions 1004 that, when executed by, for example, a processor, may provide the functionality described above with respect to FIGS. 1 to 8. By way of example, instructions 1004 may include at least one of: one or more instructions for generating, by a vibrator, mechanical vibration; one or more instructions for generating, by a laser beam source, a laser beam toward the hair; one or more instructions for detecting, by a photodetector, at least part of the laser beam reflected by the hair and converting an intensity of the detected part of the laser beam to an electrical signal; or one or more instructions for measuring, by a processor, condition of the hair based on the electrical signal. Thus, for example, referring to FIGS. 1 to 3, hair condition measuring device 100 or 200 may undertake one or more of the blocks shown in FIG. 7 in response to instructions 1004.

In some implementations, signal bearing medium 1002 may encompass a computer-readable medium 1006, such as, but not limited to, a hard disk drive (HDD), a Compact Disc (CD), a Digital Video Disk (DVD), a digital tape, memory, etc. In some implementations, signal bearing medium 1002 may encompass a recordable medium 1008, such as, but not limited to, memory, read/write (R/W) CDs, R/W DVDs, etc. In some implementations, signal bearing medium 1002 may encompass a communications medium 1010, such as, but not limited to, a digital and/or an analog communication medium (for example, a fiber optic cable, a waveguide, a wired communication link, a wireless communication link, etc.). Thus, for example, computer program product 1000 may be conveyed to one or more modules of hair condition measuring device 100 or 200 by an RF signal bearing medium 1002, where the signal bearing medium 1002 is conveyed by a wireless communications medium 1010 (for example, a wireless communications medium conforming with the IEEE 802.11 standard).

In some examples, a hair condition measuring device comprises a first clamp configured to clamp a first end of hair, a second clamp configured to clamp a second end of the hair, so that the hair is stretched between the first clamp and the second clamp; a vibrator configured to generate mechanical vibration such that the mechanical vibration is imparted to the hair; a light beam source configured to generate a light beam toward the hair; a photodetector configured to detect at least part of the light beam reflected by the hair and convert an intensity of the detected part of the light beam to an electrical signal; and a processor configured to measure a condition of the hair based on the electrical signal. In some examples, the processor is further configured to measure the condition of the hair by comparing a peak value of the electrical signal to a reference value. In some non-limiting examples, vibration frequencies in the range 0.1-100 Hz may be used, but other frequencies may also be used.

For example, for a hair in what may be considered a good condition, the thickness of the hair and cuticle condition may be generally uniform. When the hair is vibrated, the level of reflected light may be generally uniform, and the signal level may be approximately constant. However, for a hair that may be considered in not good condition, or damage, there may be perceptible cuticle detachment or variation in the hair thickness. For example, a hair thickness may vary by more than 10%, or more than 20%, as a function of spatial position along the length of the hair between the clamps. This may lead to variations in the signal level as a function of time. In some examples, variations may be detected by moving a position of light incidence on the hair. Variations in the signal level may be determined, as a function of one or more parameters, including and not limited to: time, light incidence position on the hair, frequency, amplitude of vibration, distortion (e.g., relative to the signal expected for a good condition hair), harmonics, and ambient conditions (such as temperature and humidity). Variations in the signal level may be converted into one or more numerical values, allowing comparison with reference numerical values associated with good and one or more not good conditions. Hence, in some examples, the presence, degree, and type of damage may be determined. In some examples, additional hair parameters such as color, thickness, and non-circular shape parameter (such as elliptical parameters) may be determined for a static hair and used in a hair damage model, or otherwise to improve accuracy of hair damage determinations.

In some examples, the distance between the clamps may be in a range of, for example and not limiting, 5 mm-100 mm. In some examples, the hair between the two claims may be a portion of a complete hair, and may not be the entire hair. In some examples, data may be collected from different portions of a hair by adjusting the position of the hair relative to the clamps, for example, to collect data (for example) from portions of a hair closer to a root, closer to an end, or in a generally middle portion of the hair.

In some examples, the light beam is a laser beam. In some examples, the light beam source may be a laser beam source (such as a laser diode) or a light emitting diode (LED). In some examples, the light beam (such as a laser beam) may be a visible or near-IR beam. In some examples, a light beam may be collimated, and/or may be focused on at least a portion of the hair using one or more lenses. In some examples, the hair condition measuring device may be configured to monitor hair damage, for example by being configured to determine the surface condition (such as uniformity) of the hair. In some examples, reference measurement data may be collected for damaged and healthy hairs, and collected data compared to the reference data to determine a condition of a hair. In some examples, the photodetector may comprise a photodiode (e.g., a p-i-n diode such as a silicon p-i-n diode), photoresistor, or other light-sensitive detector. A filter may be provided, such as a notch filter with a pass-band including the light beam wavelengths. In some examples, light reflection is detected from a vibrating strand of hair, allowing greater sensitivity for determination of hair parameters such as thickness uniformity and hair cuticle condition than light reflection from a static hair. In some examples, the amplitude and frequency of the hair vibration may be varied, and light reflection data collected at a plurality of amplitudes and/or vibration frequencies.

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure includes the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A hair condition measuring device, comprising:
   a first clamp configured to clamp a first end of hair;
   a second clamp configured to clamp a second end of the hair, so that the hair is stretched between the first clamp and the second damp;
   a vibrator configured to generate a mechanical vibration such that the mechanical vibration is imparted to the hair;
   a laser beam source configured to generate a laser beam toward the hair;
   a photodetector configured to detect at least part of the laser beam reflected by the hair and convert an intensity of the detected part of the laser beam to an electrical signal; and
   a processor configured to measure condition of the hair based on a value resulting from integrating noise components of the electrical signal.

2. The device of claim 1, wherein the processor is further configured to measure the condition of the hair by comparing a peak value of the electrical signal to a reference value.

3. The device of claim 1, wherein the processor comprises a microprocessor.

4. The device of claim 1, further comprising a display unit configured to display at least one of the electrical signal and a value indicating the condition of the hair.

5. The device of claim 1, wherein the laser beam source is configured to generate a laser beam with a wavelength of about 650 nm toward the hair.

6. The device of claim 1, further comprising:
   a first object lens configured to receive the laser beam generated from the laser beam source and focus the laser beam on the hair; and
   a second object lens configured to receive at least, part of the laser beam reflected by the hair and focus the received part of the laser beam on the photodetector.

7. The device of claim 6, further comprising:
   a one-way mirror configured to reflect at least part of the laser beam reflected by the hair,
   wherein the second object lens is configured to receive the at least part of the laser beam reflected by the one-way mirror and focus the received part of the laser beam on the photodetector.

8. The device of claim 1, wherein the vibrator is a magnetic vibrator comprising a magnet at least partially disposed inside a coil, wherein the magnet is configured to oscillate within the coil when an alternating current is applied to the coil and thereby impart the mechanical vibration to the hair.

9. The device of claim 8, wherein the animal hair is wool, mohair, cashmere, angora, fleece, fur or a combination thereof.

10. The device of claim 1, wherein the hair is a human hair or an animal hair.

11. A method of measuring hair condition, the method comprising:
  generating, by a vibrator, a mechanical vibration such that the mechanical vibration is imparted to hair being stretched between a first clamp and a second clamp;
  generating, by a laser beam source, a laser beam toward the hair;
  detecting, by a photodetector, at least part of the laser beam reflected by the hair and converting an intensity of the detected part of the laser beam to an electrical signal; and
  measuring, by a processor, condition of the hair based on a value resulting from integrating noise components of the electrical signal.

12. The method of claim 11, wherein measuring the condition of the hair comprises measuring, by the processor, the condition of the hair by comparing a peak value of the electrical signal to a reference value.

13. The method of claim 11, further comprising:
  displaying, by a display unit, at least one of the electrical signal and a value indicating the condition of the hair.

14. The method of claim 11, further comprising:
  receiving, by a first object lens, the laser beam generated from the laser beam source and focusing the laser beam on the hair; and
  receiving, by a second object lens, at least part of the laser beam reflected by the hair and focusing the received part of the laser beam on the photodetector.

15. The method of claim 14, further comprising:
  reflecting, by a one-way mirror, at least part of the laser beam reflected by the hair,
  wherein receiving, by the second object lens, the at least part of the laser beam comprises receiving, by the second object lens, the at least part of the laser beam reflected by the one-way mirror and focusing the received part of the laser beam on the photodetector.

16. A non-transitory computer-readable storage medium which stores a program operable by a hair condition measuring device, the program comprising one or more instructions for:
  generating, by a vibrator, a mechanical vibration such that the mechanical vibration is imparted to hair being stretched between a first clamp and a second clamp;
  generating, by a laser beam source, a laser beam toward the hair;
  detecting, by a photodetector, at least part of the laser beam reflected by the hair and converting an intensity of the detected part of the laser beam to an electrical signal; and
  measuring, by a processor, condition of the hair based on a value resulting from integrating noise components of the electrical signal.

17. The medium of claim 16, wherein measuring the condition of the hair comprises measuring, by the processor, the condition of the hair by comparing a peak value of, the electrical signal to a reference value.

18. The medium of claim 16, wherein the program further comprises one or more instructions for displaying, by a display unit, at least one of the electrical signal and a value indicating the condition of the hair.

19. The medium of claim 16, wherein the program further comprises one or more instructions for:
  receiving, by a first object lens, the laser beam generated from the laser beam source and focusing the laser beam on the hair; and
  receiving, by a second object lens, at least part of the laser beam reflected by the hair and focusing the received part of the laser beam on the photodetector.

20. The medium of claim 19, wherein the program further comprises one or more instructions for:
  reflecting, by a one-way mirror, at least part of the laser beam reflected by the hair,
  wherein receiving, by the second object lens, the at least part of the laser beam comprises receiving, by the second object lens, the at least part of the laser beam reflected by the one-way mirror and focusing the received part of the laser beam on the photodetector.

21. A method of manufacturing a hair condition measuring device, the method comprising:
  preparing a substrate;
  disposing a first clamp and a second clamp on the substrate, such that the first clamp is spaced apart from the second clamp, the first clamp being configured to clamp a first end of hair, and the second clamp being configured to clamp a second end of the hair, so that the hair is stretched between the first clamp and the second clamp;
  disposing a vibrator on the substrate, the vibrator being configured to generate mechanical vibration such that the mechanical vibration is imparted to the hair;
  disposing a laser beam source on the substrate, the laser beam being configured to generate a laser beam toward the hair;
  disposing a photodetector on the substrate, the photodetector being configured to detect at least part of the laser beam reflected by the hair and convert an intensity of the detected part of the laser beam to an electrical signal; and
  coupling a processor to the vibrator, the laser beam and the photodetector, the processor being configured to measure condition of the hair based on a value resulting from integrating noise components of the electrical signal.

22. The method of claim 21, wherein the processor is further configured to measure the condition of the hair by comparing a peak value of the electrical signal to a reference value.

23. The method of claim 21, wherein the processor comprises a microprocessor.

24. The method of claim 21, further comprising coupling a display unit to the processor, the display unit being configured to display at least one of the electrical signal and a value indicating the condition of the hair.

25. The method of claim 21, wherein the laser beam source is configured to generate a laser beam with a wavelength of about 650 nm toward the hair.

26. The method of claim 21, further comprising:
  disposing a first object lens between the laser beam source and the hair on the substrate, the first object lens being configured to receive the laser beam generated from the laser beam source and focus the laser beam on the hair;
  disposing a one-way mirror on the substrate, the one-way mirror being configured to refect at least part of the laser beam reflected by the hair; and
  disposing a second object lens between the one-way mirror and the photodetector on the substrate, the second object lens being configured to receive the at least part of the laser beam reflected by the one-way mirror and focus the received part of the laser beam on the photodetector.

27. The method of claim 21, wherein the vibrator is a magnetic vibrator comprising a magnet at least partially disposed inside a coil, wherein the magnet is configured to oscillate within the coil when an alternating current is applied to the coil and thereby impart the mechanical vibration to the hair.

28. The method of claim 21, wherein the hair is a human hair or an animal hair.

29. The method of claim 28, wherein the animal hair is wool, mohair, cashmere, angora, fleece, fur or a combination thereof.

* * * * *

UNITED STATES PATENT AND TRADEMARK OFFICE
CERTIFICATE OF CORRECTION

PATENT NO. : 9,855,004 B2
APPLICATION NO. : 14/631872
DATED : January 2, 2018
INVENTOR(S) : Mihara Page 1 of 1

It is certified that error appears in the above-identified patent and that said Letters Patent is hereby corrected as shown below:

In the Claims

In Column 16, Line 24, in Claim 1, delete "damp;" and insert -- clamp; --, therefor.

In Column 16, Line 52, in Claim 6, delete "least, part" and insert -- least part --, therefor.

In Column 17, Line 60, in Claim 17, delete "of, the" and insert -- of the --, therefor.

In Column 18, Line 28, in Claim 21, delete "generate mechanical" and insert -- generate a mechanical --, therefor.

In Column 18, Line 63, in Claim 26, delete "refect" and insert -- reflect --, therefor.

Signed and Sealed this
First Day of May, 2018

Andrei Iancu
*Director of the United States Patent and Trademark Office*